(12) United States Patent
Heinze et al.

(10) Patent No.: US 6,920,353 B1
(45) Date of Patent: Jul. 19, 2005

(54) CARDIAC PACEMAKER WITH ADJUSTABLE STIMULATION INTERVAL

(75) Inventors: Roland Heinze, Berlin (DE); Karl Stangl, Berlin (DE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/869,839

(22) PCT Filed: Nov. 30, 1999

(86) PCT No.: PCT/EP99/09756

§ 371 (c)(1),
(2), (4) Date: Sep. 10, 2001

(87) PCT Pub. No.: WO00/40296

PCT Pub. Date: Jul. 13, 2000

(30) Foreign Application Priority Data

Jan. 5, 1999 (DE) .......................... 199 00 690

(51) Int. Cl.[7] ............................................. A61N 1/362
(52) U.S. Cl. ......................................................... 607/5
(58) Field of Search ................................ 600/373, 374, 600/508, 509, 519; 607/9, 11, 28, 119, 122

(56) References Cited

U.S. PATENT DOCUMENTS 4,228,803 A  10/1980  Rickards
4,399,820 A   8/1983  Wirtzfeld et al.
4,870,968 A  10/1989  Wiertzfeld et al.
5,500,006 A * 3/1996  Heinze ........................ 607/24
5,824,014 A  10/1998  Thong et al.

FOREIGN PATENT DOCUMENTS

EP     0 647 454      4/1995
WO     WO 97/18010   5/1997

* cited by examiner

*Primary Examiner*—George R. Evanisko
*Assistant Examiner*—Frances P. Oropeza
(74) *Attorney, Agent, or Firm*—Schiff Hardin LLP

(57) ABSTRACT

A cardiac pacemaker has a pulse generator which emits stimulation pulses which are respectively separated by stimulation intervals and which collectively have an average duration. A modulation device alternatingly shortens and lengthens the stimulation intervals, without changing the average duration. An evaluation unit analyzes signals detected after each stimulation pulse and determines the electric restitution of the heart at the average stimulation interval duration on the basis of a measurement of the duration of the action potential. Changes in a measuring variable, associated with the duration of the action potential, caused by the modulation of the stimulation intervals is determined in a relationship to the average duration of the stimulation interval. This relationship is compared with at least one predetermined value, and the average duration of the stimulation interval is controlled on the basis of this comparison.

15 Claims, 4 Drawing Sheets

CARDIAC PACEMAKER WITH ADJUSTABLE STIMULATION INTERVAL

BACKGROUND OF THE INVENTION

1. Field of the Invention

The present invention is directed to a cardiac pacemaker, and in particular to a cardiac pacemaker wherein the stimulation interval between stimulation pulses is adjustable.

2. Description of the Prior Art

A generally known cardiac pacemaker is the so-called QT-or stimulus-T pacemaker such as is described for example in U.S. Pat. No. 4,228,803. Such a pacemaker has means with which the median stimulation frequency can be adapted to changes in physical and psychic stress.

To this end a circuit is provided which evaluates the ECG signal derived intracardially, detecting the beginning or the maximum of the T wave. Since the time interval between stimulation and the start of the T wave, the so-called stim-T interval shortens with increasing stress, the circuit delivers a physiological measuring parameter with which the stimulation frequency can be adapted to changing stresses.

The principle disadvantage of a frequency control system of this kind is due to the fact that the stim-T interval does not shorten only with an increase in stress, but shortens to a considerably greater degree through the rise of the stimulation frequency itself. Frequency control of this type correspondingly requires special measures in order to avoid positive feedback.

A further disadvantage of this system of frequency control is the fact that the measured stim-T intervals are dependent on hormonal secretions, i.e., they respond to hormones secreted by the adrenal cortex and transported via the blood circulation.

In principle, in the regulation of the stimulation frequency in cardiac pacemakers it is an essential goal to adapt the stimulation frequency not only to rising physical stresses, but also to take into account the individual myocardial capacity of the patient. This means that the stimulation frequency is increased with rising stress only as long as a rise in the heart time volume (HTV) is achieved. This is intended to prevent the myocardium from being overloaded and damaged by too high a stimulation frequency ("overpacing").

An attempt has been made to achieve this control by measuring the beat volume BV or an HTV-dependent measuring parameter, such as for example the central venous oxygenation (s02).

From PCT Application WO 89/06990 a method is known for hemodynamic optimization of the stimulation frequency, which uses the measurement of the central venous oxygenation s02, dependent on the heart time volume, in combination with a modulation of the stimulation frequency $\Delta HR$ over phases of two to four minutes. Optimization of the heart time volume is sought in that the frequency-dependent gradient of the oxygenation $AsO2/\Delta HR$ is kept within a predetermined range, which is a physiologically optimum range analogous to the gradient of the heart time volume $HTV/\Delta HR$.

This method depends on the stability and the accuracy of the s02 sensor catheter, which in practice have not proved to be sufficient, and the method has the disadvantage that on account of the necessary long change periods it is not possible in the necessary time of a few minutes to differentiate whether the measured s02 change is caused by the frequency change or by other influencing variables.

European Application 0 551 355 describes a method for modulating individual stimulation intervals in which the impedance measurement is used to detect the beat volume, in order to avoid the use of a sensor catheter to determine the heart time volume. Through the deliberate modulation of individual stimulation intervals $\Delta SI$ and the phase-specific demodulation of the impedance change $\Delta Z$, an attempt was made to suppress the influence of non-function-specific and thus disturbing parameter changes, and in addition the signal was calibrated with the aid of maximum modulation.

This method has the disadvantage that the principle of modulating individual stimulation intervals here is only used as a filtering and calibration method, i.e. as an interim step to determine the beat volume and thus the heart time volume (HTV). Optimization of the frequency control is then also sought by the optimization of the gradient $\Delta HTV/\Delta HR$ on the basis of an optimum hemodynamic characteristic curve. The determination of the beat volume, despite an improvement in the signal-to-noise-ratio as a result of the individual pulse modulation, has in practice still proved too inaccurate to be able to carry out reliable hemodynamic optimization. This means that optimization of the stimulation by controlling the heart time volume has in practice been problematic, since either the specific sensor catheters for measuring the beat volume or the HTV-dependent measuring parameters still have no adequate long-term stability, or measurements of the beat volume using standard catheters via the impedance are not sufficiently reliable. Moreover the evaluation becomes very complex since the mechanical transmission functions also detected and which falsify the measuring result must also be taken into account.

SUMMARY OF THE INVENTION

An object of the invention is to provide a cardiac pacemaker which renders possible quick and accurate regulation of the stimulation frequency or respectively of the duration of the stimulation interval, and overloading by too high a stimulation frequency is avoided.

The above object is achieved in accordance with the invention in a cardiac pacemaker having a pulse generator which emits stimulation pulses respectively separated by stimulation pulses respectively separated by stimulation intervals, each having a stimulation interval duration, and which collectively have an average duration, and a lead connected to the pulse generator which is adapted to deliver the stimulation pulses to a heart as well as to receive a signal containing action potential information from the heart, a modulation device connected to the pulse generator which alternatingly shortens and lengthens the stimulation interval without change the average duration, thereby cause the pulse generator to emit modulated stimulation pulses, a detector connected to the lead to detect the signal received from the heart after each modulated stimulation pulse, and an evaluation unit connected to the detector for analyzing the detector output therefrom. The evaluation unit determines the electric restitution of the heart at the average stimulation interval duration by measuring the duration of the action potential in the detector output. The evaluation unit selects a measuring variable associated with the action potential duration and identifies changes in the measuring variable caused by modulation of the stimulation intervals, relative to the average duration of the stimulation intervals, and compares the relationship between the measuring variable and the average duration to at least one predetermined value. Dependent on the result of this comparison, the average duration of the stimulation interval is controlled.

The cardiac pacemaker according to the invention which has an individually optimized regulation of the duration of the stimulation interval, avoids the necessity of determining a BV- or HTV-dependent measuring parameter and makes possible, through evaluation of the electric restitution or of the gradient of the electric restitution with the aid of the standard detection of the endocardiac ECG, a regulation of the stimulation frequency or of the duration of the stimulation interval by means of a function parameter of the heart, which directly reproduces the stress state of the patient, changes in the capacity of the myocardium and acute worsening of myocardial performance being taken into account in the frequency adaptation. Here the modulation of individual stimulation intervals is carried out in such a way that the average adjusted interval duration does not change.

The modulation of the stimulation intervals by a positive value and a negative value is carried out continuously as well as at an interval of a number of pulses with periodic repetition.

It was found that the electric restitution curve which is determined by measuring the duration of action potential, is equivalent to that which is defined by measuring the QT or the stim-T interval of the electrocardiogram.

Furthermore it has been shown that the analysis of the load- and frequency-dependent modulation of the stim-T interval is sufficiently reliable if the modulation of an individual stimulation interval gives the inequality ESI (Extrasystolic Interval)<600ms with ΔESI/BCL>10% (BCL =basic cycle length).

As the evaluation variable of the electric restitution, (advantageously a dimensionless variable), the gradient (ERG) or the relative change in the electric restitution can be used, for example, in order to achieve load-dependent control. This is possible because this gradient coincides with the rise in the physical load, while it rises with increasing stimulation frequency. Moreover it was also found that the change reaction is based mainly on a change in the time constants of the exponential restitution function and this time constant reacts substantially more quickly and more strongly to changes in the load and the frequency than does the stim-T interval in a control system according to the prior art.

Furthermore the control system according to the invention can be used well in cases of acute ischemia since the electric restitution reflects the myocardial conditions. The time constant of the exponential electric restitution, and also the gradient of same, rises with the ischemia. According to the invention this causes a reduction in the stimulation frequency.

The control system according to the invention using a single pulse modulation and detection of the electric restitution causes a quick and accurate regulation of the stimulation frequency, since the electric restitution is controlled mainly by a quick reaction mechanism controlled by neurons.

DESCRIPTION OF THE PREFERRED EMBODIMENTS

The dependence of the duration of the action potential AP of the myocardium as a function parameter of the duration of the diastole $t_d$ is designated as electric restitution. If this is spontaneously changed during a single heart cycle, for example through an extrasystole, then the action potential or its duration changes. The duration of the action potential is defined by the interval between the beginning of the stimulation and the time at which the action potential has sunk by 90%, and it decreases if the time interval between two successive stimulation pulses becomes smaller. Here a distinction is to be made between the APD change after an extrasystolic stimulation interval and the APD change after a change in the average or basic heart frequency (HR =1 BCL) according to prior art.

This alteration behavior after an extrasystolic stimulation interval can be described by a double exponential function which is referred to as the electric restitution curve ER.

The electric restitution curve (ERC) is thus defined as a function of the action potential duration APD of the cycle length of a previous extrasystolic stimulation pulse interval ESI, i.e. of an individual stimulation pulse interval which is changed from the basic cycle length (BCL), i.e. the average stimulation interval duration by +ΔESI, and which corresponds to the diastole.

The function can be described as $$ER\ APD(ESI) = APD_{p1}(1 - A1 * \exp(-t_d/T1) - A2 * \exp(-t_d/T2)).$$

Herein, $APD_{p1}$ is the plateau value, A1 and T1 are the amplitude and time constant of the quick phase of the restitution and A2 and T2 are the amplitude and time constant of the slow phase of the restitution.

The distinction in the approximate equation between a slow and a quick portion in the exponential rise of the restitution curve takes into account the fact that functions of the myocardium or of the myocardial cell are determined at the cell membrane like the ion exchange, i.e. both through quick autonomous regulating processes in the cell and the surrounding tissue and also through regulating processes which affect the whole heart-cardiovascular system and are controlled by the sympathetic nervous system and the corresponding gland functions.

As a measuring parameter to determine the electric restitution curve, as indicated above, in principle the action potential duration APD is determined which can be measured by electrodes. Tests have shown however that in measuring ECG also the so-called QT interval, i.e. the duration of the interval between the Q peak and the end of the T wave of the intracardiac ECG has the same restitution characteristic as the APD. When stimulating the ventricle with a cardiac pacemaker it is more expedient to measure, instead of the QT interval as the measuring interval, the stim-T interval STI, i.e. the interval between stimulation pulse and T wave.

Figure 1:
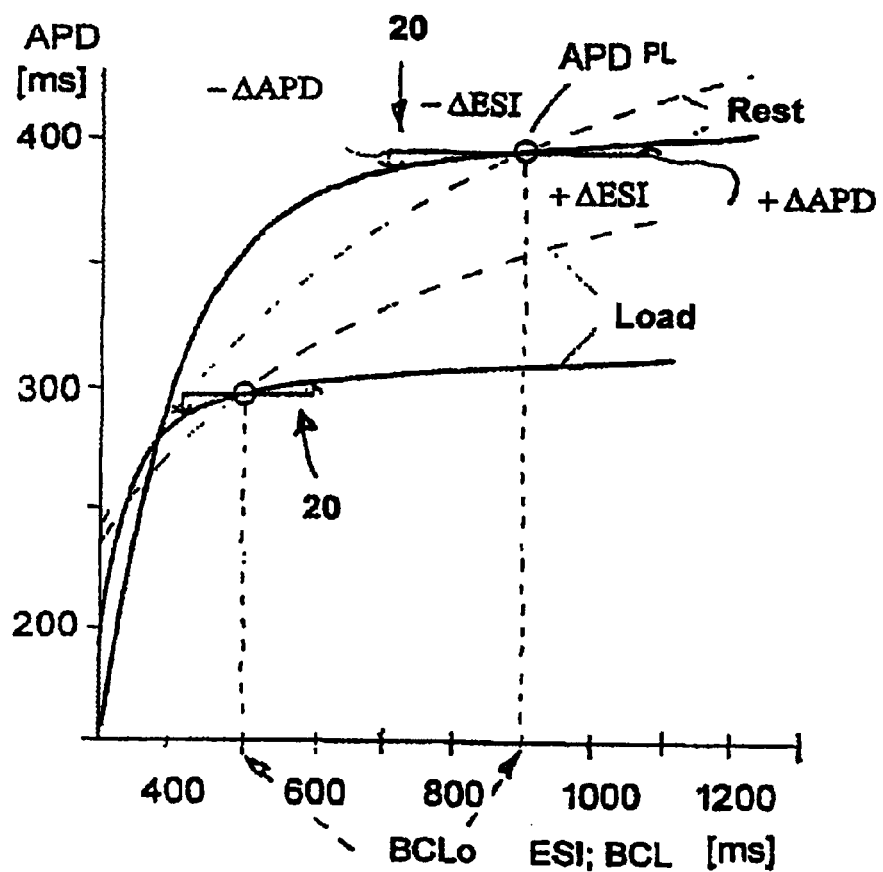
FIG. 1 shows the characteristic course of an electric restitution curve of a normal healthy myocardium in a resting phase and in a load phase.

FIG. 1 shows, as the electrical restitution curve (continuous line), the course of the action potential duration APD in dependence on the length of individual extrasystolic intervals of a normal healthy myocardium for the rest phase and for a load phase. Here in both phases respectively the optimum adapted stimulation frequency HRo optimum basic cycle length BCLo=1/HRo (i.e. the average duration the stimulation interval) was changed in individual extrasystolic stimulation intervals ESI and then the corresponding change in the action potential duration APD was measured. The restitution curves thus produced correspond to the exponential functions described by the above equation. The optimum basic cycle length BCLo for rest (90 ms) and for a load (500 ms) are represented by the broken arrows, i.e. the respective basic cycle length or average interval duration was altered by $\pm\Delta ESI$ to form extrasystolic intervals, and respectively as the reaction the action potential duration or the QT- or stim-T interval was measured as the measuring parameter. Here mean durations of the stimulation interval were alternately shortened and prolonged by positive and negative $\Delta ESI$ values that the adjusted average interval duration remains the same. Preferably the $\pm\Delta ESI$ remains the same during a change, i.e. the interval duration is shortened and prolonged by the same value. The change can be repeated periodically at an interval of a number of pulses, however it can also be carried out continuously, i.e. each stimulation pulse is alternately shortened or prolonged.

The broken lines in FIG. 1 represent the curves of the QT or stim-T intervals of an ECG with continuous alteration of the basic cycle length, or respectively with continuous modulation, which is used for example in a QT pacemaker according to prior art. As can be recognized, these characteristic curves are clearly different from the electric restitution curves with a differing load, and with increasing load, in addition to a reduction of the plateau value of the respective curve with a corresponding displacement to the left also a steeper rise in the curve was measured.

The restitution curve can now be used for physiological control of the stimulation frequency HR, it being essential, as mentioned, that both the plateau value $APD_{p1}$ and the time constants T1 and T2 are dependent on the pulse frequency HR and the level of myocardial efficiency. The stimulation frequency should therefore be so adjusted that the stimulation interval lies in the region of the plateau value $APD_{p1}$, with any load.

In order to be able to use a simpler variable for the regulation, advantageously not directly the region around the plateau value itself is selected but the gradient of the restitution curve. The gradient of the restitution curve in the respective optimum operating point, which is given by the optimum basic cycle length BCLo arises in that the extrasystolic interval ESI is altered as a percentage ($\Delta ESI/BOL$) by a defined positive $+\Delta ESI$ and/or negative value $-\Delta ESI$ and the resulting change in the action potential duration $+\Delta APD$ or $-\Delta APD$, shown by arrows 20 in FIG. 1, is measured. If this gradient of the electric restitution ERG $=+\Delta APD/+\Delta ESI$ or ERG $=-\Delta APD/-\Delta ESI$ is applied as a function of the stimulation frequency HR for the rest phase and a load phase, the course represented in FIG. 2 arises.

Figure 2:
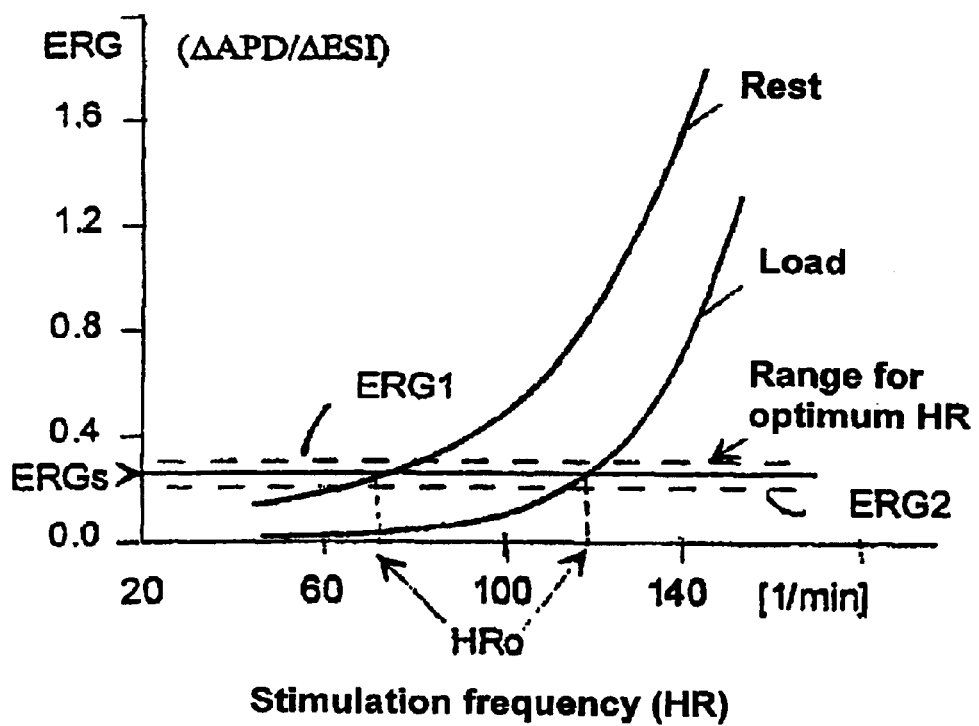
FIG. 2 shows characteristic curves for the electric restitution gradient as a function of the stimulation frequency in the rest phase and the load phase.

FIG. 2 shows that the exponential rise of the gradient of the electric restitution ERG as a function of a rising stimulation frequency HR with rising load is displaced to the right. It can be recognized that in the respective optimum heart frequency, the associated ERGo values, which correspond to the plateau values $APD_{p1}$ in FIG. 1, have approximately the same level, however the values can also be different. These values can be selected in a frequency control system as set values of the gradient of the electric restitution ERG, a region around the set value ERG being given in FIG. 2 as a range for an optimum stimulation frequency HR, which is delimited by the threshold values ERG1 and ERG2.

It is also conceivable that the gradient of the electric restitution ERG is determined from the difference between the positive and negative changes in the action potential duration in relation to the positive and negative interval changes, namely with ERG$[(+\Delta APD)-(-\Delta APD)]/\{(+\Delta ESI)-(-\Delta ESI)\}$.

On the basis of FIGS. 1 and 2 it can be recognized that the electric restitution function or its gradient ERG offers the precondition for regulating the stimulation frequency since the gradient of the electric restitution ERG reacts with an increase in the stimulation frequency conversely to the rise in the physical stress, and has within a physiologically fixed defined region an optimum value ERGo for each stress situation. From the ERG characteristic curve according to FIG. 2 it can be recognized that in the frequency control too high a stimulation frequency (overpacing) is avoided in principle.

Figure 3:
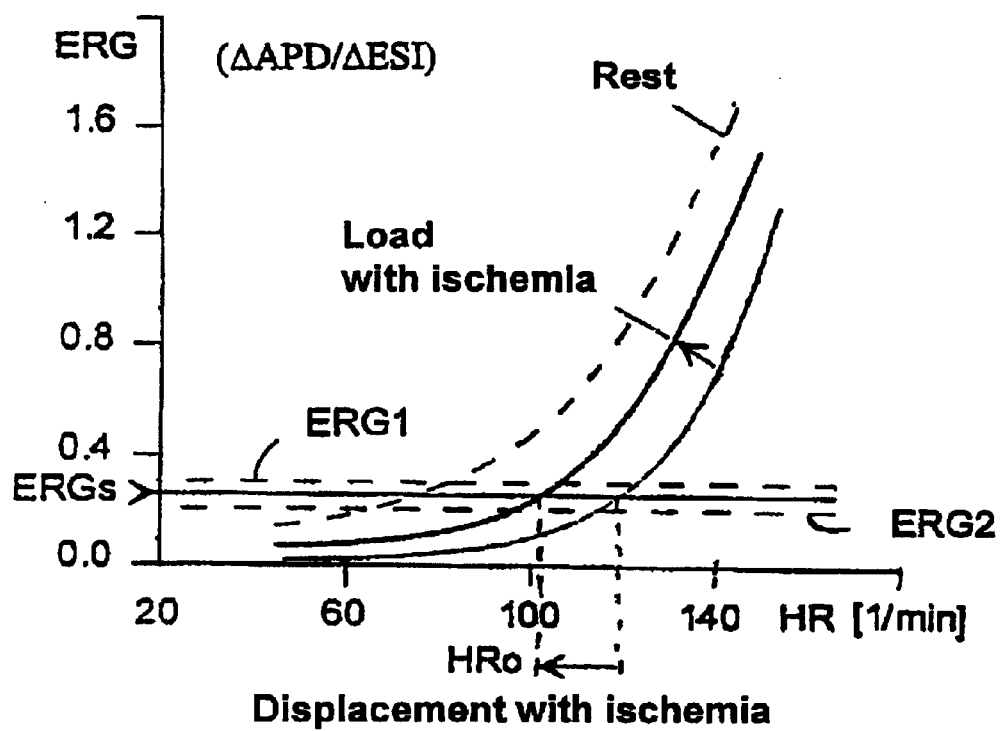
FIG. 3 shows characteristic curves of the gradient of the electric restitution dependent on the stimulation frequency given the occurrence of ischemia.

However it is also apparent that a possible acute worsening in myocardial performance in patients can occur and can be taken into account in the adaptation of the frequency. In FIG. 3 is represented the gradient of the electric restitution via the stimulation frequency for a case in which a worsening of the myocardial performance occurs through ischemia. FIG. 3 shows that the lengthening of the stim-T interval on the occurrence of an ischemia displaces the ERG curve to the left in a case of stress, i.e. the gradient of the electric restitution reacts on a drop in the myocardial capacity as in a drop in physical stress. As a result of this, the optimum stimulation frequency PRo is reduced and thus the pre-eminent requirement is met that the ERG-dependent frequency control system prevents overpacing in a myocardium which is deteriorating pathologically.

In another example, instead of the gradient, the relative change in the electric restitution can be used by forming the quotient $\Delta APD/\Delta ESI$, in each case also the averages values being able to be determined over a number of changes cycles.

Figure 4:
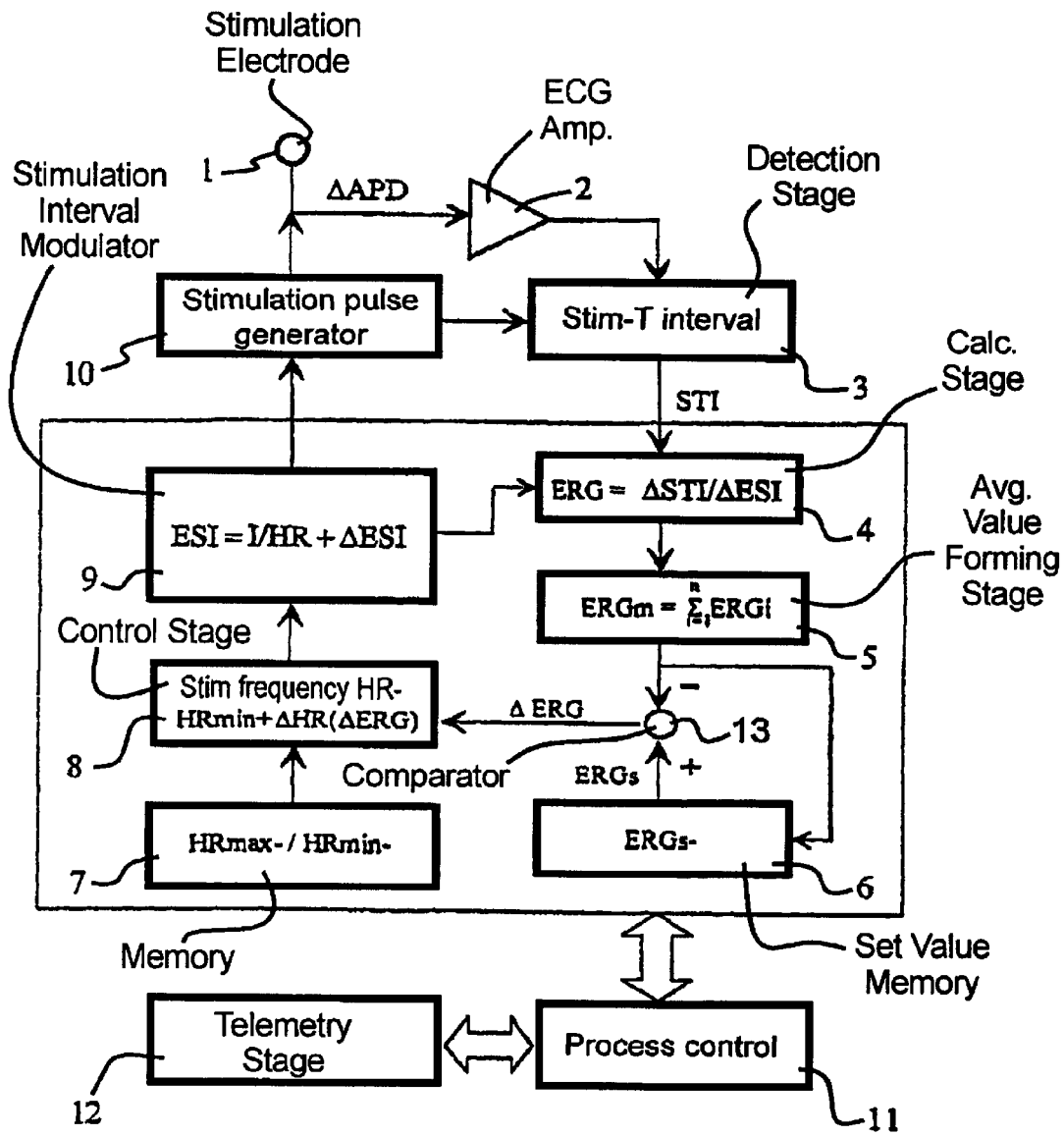
FIG. 4 is a block diagram of an embodiment of a cardiac pacemaker constructed and operating in accordance with the principles of the present invention.

In FIG. 4 is represented an embodiment of a cardiac 10 pacemaker, with which frequency control is used in dependence on the gradients of the electric restitution function ERG.

The functional blocks required for controlling frequency or the stimulation interval in dependence on the ERG are represented in the bordered area. As other functional blocks, which part of the standard equipment of a normal QT pacemaker, a simulation electrode 1 and a the stimulation pulse generator 10 supplying the stimulation electrode 1 are provided. Furthermore an ECG amplifier 2 is connected on the one hand to the stimulation electrode 1 and on the other hand to a detection stage for detecting the stim-T interval as a measuring variable. Moreover such a system contains a microprocessor, which can be programmed via a telemetry stage 12, with a process control 11.

The functional blocks of the frequency control system are an HRmax/HRmin memory 7 to store the limit values of the stimulation frequency, a control stage 8 connected to the memory, to which stage a control variable $\Delta ERG$ is supplied, a stimulation interval modulator 9 to fix and modulate the stimulation interval and which is connected to the stimulation pulse generator 10. Furthermore a calculation stage 4 is provided which receives a signal from the detection stage 3 and from the modulator 9, and a stage 5 to form the average value, a set value memory 6 and a set/actual value comparator 13.

The functioning of the cardiac pacemaker follows. The stimulation pulse generator 10 supplies a stimulation pulse to the stimulation electrode and the ECG amplifier amplifies the intracardial ECG signal derived via stimulation electrode 1. From this amplified signal, the detection stage 3 analyses the interval duration STI between the stimulation pulse and the T wave that corresponds to the QT interval or the action potential duration. In the calculation stage 4, the gradient of the electric restitution ERG is calculated, however others the above-mentioned variables can also be used. To this end first of all, triggered by the modulator 9, the change $\pm\Delta STI$ is calculated, with the stim-T interval value supplied by the detection stage, which change has been caused by the change ΔESI in the stimulation interval, and then the quotient ERG =ΔSTI/ΔESI is determined. In the average value stage 5, the average value ERGm of the ERG values is calculated over a number of change cycles. With the arrow from the exit of the average value stage 5 to the set value memory 6 indicated that the ERGm value, which in the body's rest state is measured at a average stimulation frequency of roughly 90/min, is stored as the set value.

In the set value/actual value comparator 13, the difference between the average value of the gradient of the electric restitution ERGs and the set value ERGs is formed, and is given as the difference value ΔERG to the control stage 8, the latter being used to adjust the average stimulation frequency $HR_0$. This is calculated for example with the aid of the following functions:

$$HRo = HRmin + k * \Delta ERG,$$

wherein HR is regulated that HR is <HRmax. Here HRmin and HRmax are, minimum or maximum frequencies which can be predetermined by external programming and stored in the memory 7, and k is a proportionality factor. HRmin is generally predetermined by the optimum average stimulation frequency HRo in the rest state. The basic frequency HRo thus determined is supplied to the modulation stage 9, in which the basic cycle length BOL =1/HRo is modulated periodically with an interval change ±ΔESI and the resulting stimulation interval ESI =BCLo +ΔESI is formed. In the following stimulation pulse generator 10, the stimulation pulse is then output in dependence on the ESI value. The regulation is repeated until the value ΔERG is zero.

In the above-described value, as the set value for the gradient of the electric restitution ERGs, the level was selected which arises for the individual load curves according to FIG. 2 at the optimum stimulation frequency HRo, control fluctuations between the values ERG1 and ERG2 being admitted. The set value ERGs can however also be automatically adapted to longer-term fluctuations of the restitution gradient with the aid of a second measuring parameter, independent of the modulation, with which parameter it is possible to recognize the rest state of the patient. In the rest phase then the minimum stimulation rate HRmin is automatically adjusted and the set value ERGs is adapted to the restitution gradient measured at rest. In this manner, the set value is "recalibrated". The measuring parameter which is independent of the modulation can be supplied for example by a mechanical movement sensor. The set value can also be adjusted in dependence on the frequency, for example it can be fixed during the rest state and then provided with a frequency-dependent slope.

Although modifications and changes may be suggested by those skilled in the art, it is the intention of the inventors to embody within the patent warranted hereon all changes and modifications as reasonably and properly come within the scope of their contribution to the art.

We claim:

1. A cardiac pacemaker comprising:
    a pulse generator which emits stimulation pulses respectively separated by stimulation intervals, each having a stimulation interval duration and collectively having an average duration;
    a lead connected to said pulse generator and adapted to deliver said stimulation pulses to a heart and to receive a signal containing action potential information from the heart;
    a modulation device connected to said pulse generator which alternatingly shortens and lengthens said stimulation interval duration without changing said average duration, thereby causing said pulse generator to emit modulated stimulation pulses;
    a detector connected to said lead to detect said signal after each modulated stimulation pulse, thereby producing a detector output;
    an evaluation unit having access to an electric restitution curve, said evaluation unit being connected to said detector for analyzing said detector output to determine an electric restitution of said heart, from said electric restitution curve, at the average duration by measuring a duration of said action potential from said action potential information, said action potential duration having a measuring variable associated therewith, and for identifying a relationship between changes in said measuring variable, caused by modulation of said stimulation interval, and said average duration, and for comparing said relationship to at least one predetermined value to obtain a comparison result; and
    said modulation device controlling said average duration dependent on said comparison result.

2. A cardiac pacemaker as claimed in claim 1 wherein said modulation device operates at periodic intervals to cause said pulse generator to emit said modulated stimulation pulses.

3. A cardiac pacemaker as claimed in claim 1 wherein said modulation device operates continuously to cause said pulse generator to emit said modulation stimulation pulses.

4. A cardiac pacemaker as claimed in claim 1 wherein said measuring variable is selected from the group consisting of an actual duration of the action potential of the myocardium of the heart, a time interval between a modulated stimulation pulse and a following T wave, and a time interval between a QRS and a T wave each following a modulated stimulation pulse.

5. A cardiac pacemaker as claimed in claim 1 wherein said evaluation unit forms an average of said measuring variable over a plurality of stimulation intervals.

6. A cardiac pacemaker as claimed in claim 1 comprising storing said changes of said measuring variable over a plurality of change cycles.

7. A cardiac pacemaker as claimed in claim 1 wherein said evaluation unit, for identifying said change in said measuring variable, employs a dimensionless variable of said electric restitution.

8. A cardiac pacemaker as claimed in claim 7 wherein said evaluation unit employs a gradient of said electric restitution as said dimensionless variable, calculated by forming a quotient between a change of said measuring variable and a change of said stimulation interval caused by said modulation device.

9. A cardiac pacemaker as claimed in claim 8 wherein said predetermined value is selected dependent on said gradient during a resting state of a body in which said heart is disposed.

10. A cardiac pacemaker as claimed in claim 7 wherein said evaluation unit, as said dimensionless variable, calculates a relative change in said electric restitution by forming a quotient between a change in said measuring variable and a previous value of said measuring variable.

11. A cardiac pacemaker as claimed in claim 10 wherein said predetermined value is selected dependent on said relative change during a resting state of a body in which said heart is disposed.

12. A cardiac pacemaker as claimed in claim 1 wherein said evaluation unit calculates an average value of said measuring variable over a plurality of stimulation intervals and wherein said average duration of said stimulation interval is fixed by external programming to a value obtained during a resting state of a body in which said heart is disposed, and wherein said fixed interval is stored as said predetermined value.

13. A cardiac pacemaker as claimed in claim 12 further comprising a sensor which identifies said state of rest, and wherein said evaluation unit causes said stored value of said stimulation interval to be used by said pulse generator during said state of rest.

14. A cardiac pacemaker as claimed in claim 1 wherein said evaluation unit alters said predetermined value in dependence on a duration of said stimulation interval.

15. A cardiac pacemaker as claimed in claim 1 wherein said evaluation device operates said modulation unit to control said average duration by increasing said average duration if a difference between a gradient of said electric restitution and said predetermined value falls below a negative threshold value, and decreases said average duration if said difference exceeds a positive threshold value.

* * * * *